United States Patent
Ikai et al.

[11] Patent Number: 6,156,941
[45] Date of Patent: Dec. 5, 2000

[54] PROCESS FOR PRODUCING 1,2-PROPANEDIOL

[75] Inventors: Kousei Ikai; Naotaka Kameyama; Yoshiro Furukawa; Masafumi Mikami, all of Hyogo, Japan

[73] Assignee: Daiso Co., Ltd., Osaka, Japan

[21] Appl. No.: 09/423,980

[22] PCT Filed: May 18, 1998

[86] PCT No.: PCT/JP98/02166

§ 371 Date: Dec. 20, 1999

§ 102(e) Date: Dec. 20, 1999

[87] PCT Pub. No.: WO98/52893

PCT Pub. Date: Nov. 26, 1998

[30] Foreign Application Priority Data

May 19, 1997 [JP] Japan .................................. 9-128447

[51] Int. Cl.[7] .................................................. C07C 31/18
[52] U.S. Cl. ............................................................ 568/862
[58] Field of Search .............................................. 568/862

[56] References Cited

U.S. PATENT DOCUMENTS 5,616,817 4/1997 Schuster et al. .

FOREIGN PATENT DOCUMENTS

| 1-146835 | 6/1989 | Japan . |
| 6-30790 | 2/1994 | Japan . |
| 7-59592 | 3/1995 | Japan . |
| 8-208541 | 8/1996 | Japan . |

OTHER PUBLICATIONS

Biochem. Z., 293 (1935) and English abstracts thereof.

J. Am. Chem. Soc. 1985, 107, 5210–5219, *Diethoxytriphenylphosphorane: A Mild, Regioselective Cyclodehydrating Reagent for Conversion of Diols to Cyclic Ethers: Stereochemistry, Synthetic Utility and Scope*, Philip L. Robinson et al.

J. Am. Chem. Soc. 1988, 110, 629–631, *Homogeneous Asymmetric Hudrogenation of Functional Keytones*, M. Kitamura et al.

*Primary Examiner*—James H. Reamer
*Attorney, Agent, or Firm*—Armstrong, Westerman, Hattori, McLeland & Naughton

[57] ABSTRACT

The present invention provides a process for obtaining 1,2-propanediol or optically active substances thereof in high yields and at a low cost using readily available starting materials. According to the process of the present invention, 3-halogeno-1,2-propanediol of the general formula [I] is catalytically hydrogenated in an alcoholic solvent having two or more carbon atoms in the presence of a base of an equivalent or less to the starting material to give 1,2-propanediol of the formula [II]. In the formula [I], X stands for a halogen atom.

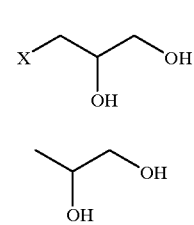

9 Claims, No Drawings

PROCESS FOR PRODUCING 1,2-PROPANEDIOL

TECHNICAL FIELD

The present invention relates to a process for producing 1,2-propanediol, particularly, optically active substances thereof, which are useful compounds as a synthetic intermediate of medicines, agricultural chemicals and the like.

BACKGROUND OF THE INVENTION 1,2-Propanediol is a known substance as an industrially useful compound. As a conventional process for producing the compound, it is reported that 1) 3-chloro-1,2-propanediol is converted into glycidol in a solution of potassium hydroxide-methanol and then glycidol is catalytically hydrogenated to give the object substance (M. Ochiai, Biochem. Z., 293 (1935)).

Known processes for producing optically active substances of 1, 2-propanediol are 2) reduction of natural ethyl lactate (J. Amer. Chem. Soc., 107, 5210 (1985)), 3) reduction of hydroxyacetone in the presence of a chiral catalyst (J. Amer. Chem. Soc., 110, 629 (1988)), 4) asymmetry reduction of hydroxyacetone with yeast (Japanese Laid-open Patent Publication No. 059592/1995), 5) resolution of racemate with enzyme (Japanese Laid-open Patent Publication No. 030790/1994), etc.

In the case of the above-mentioned conventional processes, however, since 1.2 equivalents of the base is used to the starting compound in the process 1), it leads to forming by-products such as polymers and 3-methoxy-1,2-propanediol. Since it is difficult to separate these by-products from the object substance, the yield of the object substance is low (72%). Actually, when the reaction 1) was carried out on a large scale, the yield was lower (47% (see Comparative Example 2 mentioned later)). The process 2) has disadvantages in that both of optically active substances of 1,2-propanediol cannot arbitrarily be obtained because the starting material is a natural optically active substance and in that it is necessary to use lithium aluminium hydride, which is difficult to handle in a practical use and expensive, as a reducing agent. In the process 3), the optical purity of the obtained object substance is low (92%ee), and it needs troublesome steps wherein the optical purity is improved by recrystallization after conversion into a derivative in order to obtain the object substance having high optical purity. In the processes 4) and 5), only one optically active substance is obtained.

In view of the above-mentioned various problems, the object of the present invention is to provide a process for obtaining 1,2-propanediol or the optically active substances thereof, both are the object substance, in high yields and at a low cost, using a readily available compound as a starting material.

DISCLOSURE OF THE INVENTION

Doing studies continuously to attain the above-mentioned object, the inventors found a process for producing 1,2-propanediol, particularly, optically active substances thereof advantageously using 3-halogeno-1,2-propanediol as a starting compound and accomplished the present invention.

The present invention relates to a process for producing 1,2-propanediol characterized in that 3- halogeno-1,2-propanediol represented by the following general formula [I] is catalytically hydrogenated in an alcoholic solvent having two or more carbon atoms in the presence of a base of 0.9 to one mole with respect to one mole of 3-halogeno-1,2-propanediol to give 1,2-propanediol represented by the following formula [II]. In the general formula [I], X stands for a halogen atom.

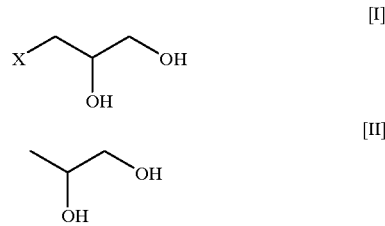

3-Halogeno-1,2-propanediol [I] can be obtained by any processes. Optically active 3-halogeno-1,2-propanediol can easily be prepared according to processes described in Japanese Examined Patent Publication Nos. 73998/1992 and 73999/1992.

The halogen atom X of 3-halogeno-1,2-propanediol [I] is preferably a chlorine atom or a bromine atom. Accordingly, preferred 3-halogeno-1,2-propanediol, which is the starting material, is 3-chloro-1,2-propanediol or 3-bromo-1,2-propanediol.

The "alcoholic solvent" means a solvent which comprises alcohol(s) having two or more carbon atoms in the present specification. Namely, the solvent can contain the other omponent(s) than alcohol(s) having two or more carbon atoms, unless the other components substantially influence the fundamental and novel characteristic of the present invention. For example, the alcoholic solvent can comprise a large part of the alcohol(s) having two or more carbon atoms and a small part of other solvent(s) which is (are) compatible with the alcohol(s). However, the larger the proportion of the other solvent(s), the m ore liable to occur are side reactions. As a result, a yield of the object substance tends to decrease. Accordingly, a range of the proportion of the other solvent(s) is decided so that the yield of the object substance is not lower than a desired value.

The hydrocarbon group of the alcohol(s) can be straight, branched or cyclic, and can have substituent(s).

The alcohol can be monohydric or polyhydric depending on a number of hydroxyl groups, and can be any of an n-alcohol, a sec-alcohol and a tert-alcohol depending on a position of the hydroxyl group.

A preferred alcoholic solvent is essentially composed of monohydric alcohol(s) having two to four carbon atoms. A particularly preferred alcoholic solvent is essentially composed of an alcohol selected from the group consisting of propanol, isopropanol, n-butanol, isobutanol, sec-butanol and tert-butanol, or combination of two or more thereof. When methanol is used as the solvent, glycidol, which forms in the reaction process, reacts with methanol to give a by-product, which lowers the yield of the object substance.

The base used in the process of the present invention can be a substance which exhibits basicity (including Lewis bases). Examples of the base are hydroxides of alkali metals or alkali earth metals such as lithium hydroxide, sodium hydroxide, potassium hydroxide, magnesium hydroxide and calcium hydroxide: carbonates of alkali metals or alkali earth metals such as lithium carbonate, sodium carbonate, potassium carbonate, magnesium carbonate and calcium carbonate; hydrogencarbonates of alkali metals such as lithium hydrogencarbonate, sodium hydrogencarbonate and potassium hydrogencarbonate; hydrides such as sodium hydride, potassium hydride and calcium hydride; alkali alkoxides such as sodium methylate, sodium ethylate, potassium methylate, potassium ethylate, potassium t-butoxide: and amines such as triethylamine, pyridine, 2, 6-lutidine, dimethylaniline, diazabicycloundecene and diazabicyclononene. These can be used individually or in combination. Among them, hydroxides of alkali metals, particularly sodium hydroxide and potassium hydroxide are preferable.

An amount of the base used is 0.9 to one mole, preferably 0.95 to one mole with respect to one mole of the starting material 3-halogeno-1,2-propanediol [I]. When the amount of the base is more than one mole with respect to one mole of the starting material, undesirable by-products form. On the contrary, when the amount of the base is less than 0.9 mole, 3-halogeno-1,2-propanediol [I] remains and the yield of 1,2-propanediol decreases.

A catalyst used in catalytically hydrogenating 3-halogeno-1, 2-propanediol in the process of the present invention can be a usual catalyst for catalytic hydrogenation. Examples of the catalyst are palladium-carbon, Raney nickel, platinum oxide, etc. Palladium-carbon is preferable among them.

An amount of the catalyst used is suitably 1 to 100 g with respect to one mole of 3-halogeno-1,2-propanediol [I]. When the amount of the catalyst used is less than 1 g to one mole of the starting material, the reaction proceeds slowly, and sometimes the practical operation cannot be carried out. On the contrary, when the amount is more than 100 g, the cost increases.

Hydrogen gas for catalytic hydrogenation can be supplied from a usual hydrogen source. Hydrogen gas in a hydrogen cylinder or ammonium formate can be used as the hydrogen source. Since removal of excess of ammonium formate after the reaction requires troublesome steps in the latter case, it is preferable to use hydrogen gas. Though a theoretical amount of hydrogen is one mole to one mole of 3-halogeno-1,2-propanediol [I], the practical amount is usually in excess of the theoretical amount, and preferably once to three times as much as the theoretical amount. It is preferable to adjust the amount of supplied hydrogen according to the state of progress of the reaction. When ammonium formate is used as the hydrogen source, it is preferable to add about 10 moles of ammonium formate to one mole of the starting material because ammonium formate is solid matter.

There are two ways which are different in the addition order of the base and catalytic hydrogenation; a process wherein the catalytical hydrogenation is carried out after the addition of the base is finished; and a process wherein the catalytic hydrogenation is carried out simultaneously with the addition of the base. Good results are obtained in both ways.

The catalytic hydrogenation can be carried out under norm al pressure and can also be carried out under elevated pressure, for example, under hydrogen pressure of 10 Kgf/$cm^2$ (gauge pressure) or lower.

Reaction temperature is preferably −20° to 80° C., and m ore preferably 0° to 50° C. When the reaction temperature is lower than −20° C., the progress of the reaction is slow, and viscosity of a reaction liquid tends to increase. On the contrary, when the reaction temperature is higher than 80° C., a dimer of the starting material, etc. form, and the yield of 1,2-propanediol is apt to decrease.

After the reaction is completed, the object substance is obtained by the conventional method. For example, insoluble matter such as the catalyst is filtered out, an excessive solvent is evaporated under reduced pressure, and the obtained residue is usually treated, e.g. distilled to give object substance 1,2-propanediol. The above-mentioned reaction is carried out using 3-halogeno-1,2-propanediol which is the optically active substance as a starting material to give desired optically active 1,2-propanediol with little decrease in optical purity.

A reaction mechanism of the process of the present invention is not definite. However, it is considered that a successive reactions occur wherein 3-halogeno-1,2-propanediol [I] is converted into glycidol with the base and then 1,2-propanediol [II] is formed by the catalytic hydrogenation.

BEST MODE FOR CARRYING OUT THE INVENTION

The present invention is practically described by Examples below, but the present invention is not limited to these Examples. Comparative Example 1 is an example wherein methanol is used as a solvent. Comparative Example 2 is an example wherein methanol is used as a solvent and an excessive base is used to a starting material. Comparative Example 3 is an example wherein isopropanol is used as a solvent and the excessive base is used to the starting material.

EXAMPLE 1 a) In a flask of 200 ml, 10 g (90.5 mmol) of 3-chloro-1, 2-propanediol was dissolved in 50 ml of isopropanol. To the solution was added 7.2 g (86.4 mmol) of a 48% aqueous NaOH solution dropwise in an ice bath over 30 minutes. The mixture was stirred at 25° C. for 30 minutes, and then 1 g of 10% palladium-carbon (50% wet product) was added thereto. The atmosphere in the flask was replaced with hydrogen, and the mixture was stirred at 40° C. for further three hours.

b) Then the reaction mixture was filtered to remove insoluble matter, the filtrate was concentrated under reduced pressure, and the residue is purified by distillation to give 6.0 g (yield 87.2%) of 1, 2-propanediol.

EXAMPLE 2

In an autoclave of 1000 ml, 50 g (0.45 mol, optical purity 99.6%ee) of (S)-3-chloro-1,2-propanediol was dissolved in 250 ml of isopropanol. To the solution was added 35.8 g (0.43 mol) of a 48% aqueous NaOH solution dropwise in an ice bath over 30 minutes. The mixture was stirred at 25° C. for 30 minutes, and then 5 g of 10% palladium-carbon (50% wet product) was added thereto. Then hydrogen gas was supplied to the autoclave so that hydrogen pressure was always kept at 5 Kgf/$cm^2$.and the mixture was stirred at 25° C. for further two hours.

Next the same operation as in the step b) of Example 1 was repeated to give 31.8 g, (yield 92.4%, optical purity 99.3%ee) of (R)-1, 2-propanediol.

EXAMPLE 3

In a flask of five liters, 500 g (4.52 mol. optical purity 98.2%ee) of (R)-3-chloro-1,2-propanediol was dissolved in 2240 ml of isopropanol. To the solution was added 360 g (4.32 mol) of a 48% aqueous NaOH solution dropwise in an ice bath over one hour. The mixture was stirred at 25° C. for 30 minutes, and then 49 g of 10% palladium-carbon (50% wet product) was added thereto. The atmosphere in the flask was replaced with hydrogen, and the liquid was stirred. The stirring was continued at 40° C. for further seven hours.

Then the same operation as in the step b) of Example 1 was repeated to give 313 g (yield 91.0%, optical purity 98.0%ee) of (S)-1, 2-propanediol.

EXAMPLE 4

In a flask of five liters, 500 g (4.52 mol, optical purity 99.6%ee) of (S)-3-chloro-1,2-propanediol was dissolved in 2240 ml of isopropanol. To the solution was added 49 g of 10% palladium-carbon (50% wet product). The atmosphere in the flask was replaced with hydrogen, 360 g (4.32 mol) of a 48% aqueous NaOH solution was added to the mixture dropwise with stirring at 40° C. over 10 hours. and the mixture was stirred for further one hour.

Then the same operation as in the step b) of Example 1 was repeated to give 310 g (yield 90.0 %, optical purity 99.2%ee) of (R)-1, 2-propanediol.

Comparative Example 1

In a flask of 30 liters, 3.75 kg (33.9 mol, optical purity 99.6%ee) of (S)-3-chloro-1,2-propanediol was dissolved in 14 liters of methanol. To the solution was added 2.70 kg (32.4 mol) of a 48% aqueous NaOH solution dropwise in an ice bath over two hours. The mixture was stirred at 25° C. for one hour, and then 375 g of 10% palladium-carbon (50% wet product) was added thereto. The atmosphere in the flask was replaced with hydrogen, and the mixture was stirred at 40° C. for further 11 hours.

Then the same operation as in the step b) of Example 1 was repeated to give 1.62 kg (yield 62.8%, optical purity 99.0%ee) of (R)- 1,2-propanediol.

Comparative Example 2

In a flask of 10 liters, 500 g (4.52 mol, optical purity 99.6%ee) of (S)-3-chloro-1,2-propanediol was dissolved in 2.5 liters of methanol. To the solution was added 1.5 liters (5.36 mol) of a 20% KOH/methanol solution dropwise in an ice bath over one hour. The mixture was stirred at 25° C. for 30 minutes, and then 50 g of 10% palladium-carbon (50% wet product) was added thereto. The atmosphere in the flask was replaced with hydrogen, and the mixture was stirred at 40° C. for further eight hours.

Then the same operation as in the step b) of Example 1 was repeated to give 162 g (yield 47.1%, optical purity 98.8%ee) of (R)-1, 2-propanediol.

Comparative Example 3

In a flask of 1000 ml, 50 (0.45 mol, optical purity 99.6%ee) of (S)-3-chloro-1,2-propanediol was dissolved in 250 ml of isopropanol. To the solution was added 45 kg (0.54 mol) of a 48% aqueous NaOH solution dropwise in an ice bath over 30 minutes. The mixture was stirred at 25° C. for 30 minutes, and then 5 g of 10% palladium-carbon (50% wet product) was added thereto. The atmosphere in the flask was replaced with hydrogen, and the mixture was stirred at 40° C. for further four hours.

Then the same operation as in the step b) of Example 1 was repeated to give 22.4 g (yield 66.4%, optical purity 99.6%ee) of (R)-1, 2-propanediol.

Industrial Applicability

The present invention provides a process for advantageously obtaining 1,2-propanediol, which is a useful compound as a synthetic intermediate of medicines, agricultural chemicals, etc.

According to the present invention, 1,2-propanediol can be obtained in a higher yield at a lower cost compared with conventional methods. In particular, optically active substances can be obtained without decreasing purity thereof.

What is claimed is:

1. A process for producing 1,2-propanediol characterized in that 3-halogeno-1,2-propanediol represented by the general formula [I] wherein X stands for a halogen atom is catalytically hydrogenated in an alcoholic solvent having two to four carbon atoms in the presence of a base of 0.9 to one mole with respect to one mole of 3-halogeno-1,2-propanediol to give 1,2-propanediol represented by the formula [II]

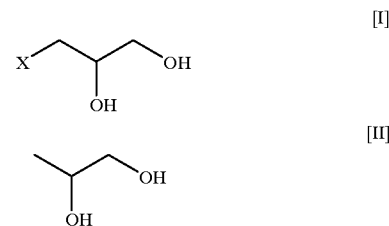

wherein X stands for a halogen atom, and said base being selected from the group consisting of hydroxides of alkali metals or alkali earth metals, carbonates of alkali metals or alkali earth metals, hydrogencarbonates of alkali metals, hydrides and alkali alkoxides.

2. A process for producing 1,2-propanediol as claimed in claim 1, wherein 3-halogeno-1,2-propanediol [I] is 3-chloro-1,2-propanediol or 3-bromo-1,2-propanediol.

3. A process for producing 1,2-propanediol as claimed in claim 2, wherein the alcoholic solvent is essentially composed of an alcohol selected from the group consisting of propanol, isopropanol, n-butanol, isobutanol, sec-butanol and tert-butanol or combination of two or more thereof.

4. A process for producing 1,2-propanediol as claimed in any one of claims 1 to 4, wherein the base is a hydroxide of an alkali metal.

5. A process for producing 1,2-propanediol as claimed in claim 4, wherein the hydroxide of the alkali metal is sodium hydroxide or potassium hydroxide.

6. A process for producing 1,2-propanediol as claimed in claim 5, wherein the amount of the base is one to 0.95 mole with respect to one mole of 3-halogeno-1,2-propanediol [I].

7. A process for producing 1,2-propanediol as claimed in claim 6, wherein the catalytic hydrogenation is carried out after addition of the base is finished.

8. A process for producing 1,2-propanediol as claimed in claim 6, wherein the catalytic hydrogenation is carried out simultaneously with the addition of the base.

9. A process for producing 1,2-propanediol as claimed in any one of claims 1 to 4, wherein both 3-halogeno-1,2-propanediol [I] and 1,2-propanediol [II] are optically active substances.

* * * * *